United States Patent [19]

Imai et al.

[11] 4,204,066

[45] May 20, 1980

[54] PREPARATION OF ALKYL PYRIDINES

[75] Inventors: Tamotsu Imai, Mt. Prospect; Edwin H. Homeier, Maywood, both of Ill.

[73] Assignee: UOP Inc., Des Plaines, Ill.

[21] Appl. No.: 965,670

[22] Filed: Dec. 1, 1978

[51] Int. Cl.² ............................................. C07D 213/12
[52] U.S. Cl. ................................................... 546/348
[58] Field of Search ......................................... 546/348

[56] References Cited

U.S. PATENT DOCUMENTS

| | | | |
|---|---|---|---|
| 3,679,688 | 7/1972 | Fenton | 546/348 |
| 3,679,689 | 7/1972 | Fenton | 546/348 |

*Primary Examiner*—Natalie Trousof
*Attorney, Agent, or Firm*—James R. Hoatson, Jr.; Raymond H. Nelson; William H. Page, II

[57] ABSTRACT

Alkyl pyridines may be synthesized from a mixture of ethylene, carbon monoxide, hydrogen and ammonia by reacting the mixture in the presence of metal catalyst complexes selected from the group consisting of metal phthalocyanines and metal carbonyls which act as a catalyst for the reaction at temperatures which may range from about 50° to about 300° C. and pressures ranging from about 10 atmospheres to about 300 atmospheres.

9 Claims, No Drawings

PREPARATION OF ALKYL PYRIDINES

This invention relates to a process for the synthesis of alkyl pyridines. More specifically, the invention is concerned with the process for synthesizing alkyl pyridine in which a mixture of ethylene, carbon monoxide, hydrogen and ammonia are reacted in the presence of certain catalyst compositions of matter of the type hereinafter set forth in greater detail.

Alkyl pyridines such as the isomeric dimethylpyridines, trimethylpyridines, and dimethyl ethylpyridine are useful in the chemical industry. For example, a particular dimethylpyridine such as 2,6-dimethylpyridine or, as it is also known, 2,6-lutidine, is useful in the preparation of pharmaceuticals, resins, dye stuffs, rubber accelerators, insecticides, etc., while 2,4,6-trimethylpyridine, which is also known as 2,4,6-collidine is useful as a chemical intermediate as well as a dehydrohalogenating agent.

It is therefore an object of this invention to provide a novel process for preparing alkyl pyridines.

A further object of this invention is to provide a novel process for the synthesis of alkyl pyridines from a mixture of ethylene, ammonia, carbon monoxide and hydrogen utilizing metal catalyst complexes to effect the reaction.

In one aspect an embodiment of this invention resides in a process for the preparation of an alkyl pyridine which comprises reacting a mixture of ethylene, carbon monoxide, hydrogen and ammonia in the presence of a metal catalyst complex selected from the group consisting of metal phthalocyanines and metal carbonyls at reaction conditions, and recovering the resultant alkyl pyridine.

A specific embodiment of this invention is found in a process for the preparation of an alkyl pyridine which comprises reacting a mixture of ethylene, carbon monoxide, hydrogen and ammonia in the presence of rhodium phthalocyanine tetrasulfonate at a temperature in the range of from about 50° to about 300° C. and a pressure in the range of from about 10 to about 300 atmospheres, and recovering the resultant 2-ethyl-3,4-dimethylpyridine.

Other objects and embodiments will be found in the following further detailed description of the present invention.

As hereinbefore set forth, the present invention is concerned with a process for the synthesis of alkyl pyridines. The process is effected by treating or reacting a mixture of ethylene, carbon monoxide, hydrogen and ammonia at reaction conditions in the presence of certain metal catalyst complexes. The reaction conditions which may be employed to effect the synthesis of the ethyl pyridines will include temperatures in the range of from about 50° up to about 300° C. or more and pressures which may range from about 10 atmospheres to about 300 atmospheres. While the pressures which are employed may be autogeneous, it is also contemplated within the scope of this invention that higher pressures may be employed by the addition of an inert gas such as nitrogen, helium, argon, etc., into the reaction vessel.

Examples of metal catalyst complexes which may be employed to effect the synthesis of the alkyl pyridine include transition metals of Groups IB and VIII of the Periodic Table. Specific examples of these macrocyclic compounds will include metal phthalocyanines such as cobalt phthalocyanine, cobalt phthalocyanine monosulfonate, cobalt phthalocyanine disulfonate, cobalt phthalocyanine tetrasulfonate, rhodium phthalocyanine, rhodium phthalocyanine monosulfonate, rhodium phthalocyanine disulfonate, rhodium phthalocyanine tetrasulfonate, ruthenium phthalocyanine, ruthenium phthalocyanine monosulfonate, ruthenium phthalocyanine disulfonate, ruthenium phthalocyanine tetrasulfonate, copper phthalocyanine, copper phthalocyanine monosulfonate, copper phthalocyanine disulfonate, copper phthalocyanine tetrasulfonate, chlororhodium phthalocyanine, chlororhodium phthalocyanine monosulfonate, chlororhodium phthalocyanine disulfonate, chlororhodium phthalocyanine tetrasulfonate, etc., metal carbonyls such as hexarhodiumhexadecylcarbonyl, tetrarhodiumdodecylcarbonyl, chlororhodiumcarbonyl dimer, hydridorhodiumtris(trimethylphosphene)carbonyl, hydridorhodiumtris(tri-n-butylphosphene)carbonyl, hydridorhodiumtris(triphenylphosphene)carbonyl, hydridorhodiumtris(trimethylphosphite)carbonyl, hydridorhodiumtris(triethylphosphite)carbonyl, hydridorhodiumtris(triphenylphosphite)carbonyl, tetrairidiumdodecylcarbonyl, bis(trimethylphosphino)-iridiumcarbonyl chloride, bis(triethylphosphino)iridiumcarbonyl chloride, bis(tri-n-butylphosphino)iridiumcarbonyl chloride, bis(triphenylphosphino)-iridiumcarbonyl chloride, trirutheniumdodecylcarbonyl, dicobaltoctacarbonyl, triosmiumdodecylcarbonyl, hydridocobalttetracarbonyl, cyclopentadienylcobaltdicarbonyl, bis(trimethylphosphino)dicobalthexacarbonyl, bis(triethylphosphino)dicobalthexacarbonyl, bis(tripropylphosphino)dicobalthexacarbonyl, bis(triphenylphosphino)dicobalthexacarbonyl, etc. It is to be understood that the aforementioned compounds are only representative of the type of transition metal macrocyclic compounds which may be employed as catalysts, and that the present invention is not necessarily limited thereto.

It is also contemplated within the scope of this invention that other metal compounds such as trisethylenediaminerhodium(III) chloride, cobalt carbonate, osmium trichloride, rhodium trichloride, iridium oxide, hexaammoniaruthenium(II) chloride, etc., may also be used as precursors which form the metal carbonyl complexes, although not necessarily with equivalent results.

The components of the reaction mixture, namely, ethylene, ammonia, carbon monoxide and hydrogen are present in the mixture in varying molar ratios. In the preferred embodiment of the invention, the molar ratio of ammonia to ethylene is in a range of from about 1:1 to about 5:1 moles of ammonia/mole of ethylene; the mole ratio of carbon monoxide to ethylene is in a range of from about 1:1 to about 2:1 moles of carbon monoxide/mole of ethylene; while the mole ratio of hydrogen to carbon monoxide is in a range of from about 0.5:1 to about 3:1 moles of hydrogen/mole of carbon monoxide.

The process of the present invention may be effected in any suitable manner and may comprise either a batch or continuous type operation. For example, when a batch type operation is used a quantity of the four components of the mixture, namely, ethylene, ammonia, carbon monoxide and hydrogen are charged to a pressure resistant vessel such as an autoclave utilizing the desired molar amounts of each component. The autoclave which contains a transition metal catalyst complex of the type hereinbefore set forth in greater detail, after having been sealed, is then heated to the desired operating temperature within the range of from about ambient to about 300° C. and is maintained thereat for a predetermined period of time which may range from about 0.5 up to about 4 hours or more in duration. At the end of the residence time, heating is discontinued and the autoclave allowed to return to room temperature. After reaching room temperature the excess pressure is discharged and the autoclave is opened. The reaction mixture is recovered, separated from the catalyst by conventional means such as distillation, decantation, filtration, etc., and subjected to fractional distillation whereby the various components of the reaction mixture comprising alkyl pyridines such as 2,3-dimethylpyridine, 2,4-dimethylpyridine, 2,5-dimethylpyridine, 2,6-dimethylpyridine, 2,4,6-collidine, 2-ethyl-3,4-dimethylpyridine, etc., are separated and recovered.

It is also contemplated within the scope of this invention that the process for the synthesis of alkyl pyridines may be accomplished in a continuous manner of operation. When such a type of operation is to be employed, a reaction vessel containing the desired transition metal catalyst complex is maintained at the proper operating conditions of temperature and pressure while the four components of the reaction mixture comprising ethylene, ammonia, carbon monoxide and hydrogen are continuously charged to the reaction zone. After passage over the catalyst and through the zone for a predetermined period of time, the reactor effluent is continuously withdrawn and subjected to conventional means of separation whereby the various alkyl pyridines are recovered while any unreacted starting material may be recycled to the reaction zone to form a portion of the feed stock.

The following examples are given to illustrate the process of this invention. However, it is to be understood that these examples are given merely for purposes of illustration and that the present invention is not necessarily limited thereto.

EXAMPLE I

In this example a mixture of ethylene, ammonia, carbon monoxide and hydrogen were charged to a 1 liter autoclave which contained 0.05 gram of a rhodium phthalocyanine tetrasulfonate catalyst. The reactants were charged so that the mole ratio of ammonia to ethylene was 0.437 moles of ammonia/mole of ethylene. The initial pressure of the reaction was 226 atmospheres. Thereafter the autoclave was heated to a temperature of 145° C. and maintained thereat for a period of 10 hours, the pressure dropping during the reaction period until a final pressure of 60 atmospheres was reached. At the end of the 10 hour period, heating was discontinued and the autoclave was allowed to return to room temperature. The excess pressure was discharged, the autoclave was opened and the reaction products were subjected to preparative gas-liquid chromatography followed by infrared and nuclear magnetic resonance spectroscopy. The analysis determined that there had been a 36% conversion of ethylene with a 44.8% selectivity to 2-ethyl-3,4-dimethylpyridine and a 29.4% selectivity to other alkyl pyridines. In addition there were minor amounts of alkyl piperadines, heavy unknowns and light unknowns.

EXAMPLE II

A reaction mixture comprising ethylene, ammonia, carbon monoxide and hydrogen were charged to a sealed autoclave containing 0.78 grams of rhodium phthalocyanine tetrasulfonate catalyst. The reactants were charged at a mole ratio of 1.3 moles of ammonia/mole of ethylene, the initial operating pressure being 253 atmospheres. The autoclave was then heated to a temperature of 145° C., although the temperature rose to 175° C. early in the run due to exotherm. The autoclave and contents thereof were maintained at a temperature of 145° C. for a period of 1.4 hours, the pressure dropping during the run until a final pressure of 128 atmospheres was reached. At the end of the 1.4 hour period heating was discontinued and the autoclave was allowed to return to room temperature. The excess pressure was discharged, the autoclave was opened and the reaction products recovered therefrom. The products were subjected to preparative gas-liquid chromatography followed by infrared, nuclear magnetic resonance and mass spectroscopies. The analysis determined that there had been a 33% conversion of the ethylene with a 54.4% selectivity to 2-ethyl-3,4-dimethylpyridine and a 27.8% selectivity to other alkyl pyridines. In addition, there was an 11.8% selectivity to a mixture of alkyl piperadines and a 6.0% selectivity to light unknowns.

EXAMPLE III

In a series of experiments in which a mixture of ethylene, ammonia, carbon monoxide and hydrogen may be reacted in the presence of various methyl catalyst complexes such as cobalt phthalocyanine, chlororhodium phthalocyanine tetrasulfonate, ruthenium phthalocyanine, and copper phthalocyanine tetrasulfonate, utilizing reaction conditions similar to those set forth in the above examples, it may be determined that the products resulting from the reaction may comprise a mixture of dimethylpyridines, trimethylpyridines, and dimethyl ethylpyridines.

EXAMPLE IV

In this example a mixture of 20 grams of ammonia, 24 grams of ethylene, and 200 atmospheres of a blend of a 1:1 mole ratio of carbon monoxide and hydrogen were charged to a 1 liter autoclave which contained 0.035 gram of a chlororhodiumcarbonyl dimer catalyst. In mole ratio of ethylene to rhodium in the catalyst was 4869 moles of ethylene/mole of rhodium. The initial pressure of the reaction was 175 atmospheres. The autoclave was then heated to a temperature of about 150° C. and maintained thereat for a period of 3 hours, the pressure dropping during the reaction period until a final pressure of 150 atmospheres was reached. At the end of the 3 hour period heating was discontinued and the autoclave was allowed to return to room temperature. The excess pressure was discharged, the autoclave was opened, and the reaction products were subjected to preparative gas liquid chromatography followed by infrared and nuclear magnetic resonance spectroscopy. The analysis determined that there had been a 93.61% conversion of ethylene with a 61.6% selectivity to alkyl pyridines, mainly, 2-ethyl-3,4-dimethylpyridine.

EXAMPLE V

In like manner, a reaction mixture comprising 24 grams of ethylene, 20 grams of ammonia and 200 atmospheres of a 1:1 mole ratio blend of carbon monoxide and hydrogen were charged to a sealed autoclave containing 0.087 gram of a catalyst comprising hydridorhodiumtris(triphenylphosphene)carbonyl. The initial operating pressure was 167 atmospheres. The autoclave was then heated to a temperature of 150° C. and maintained at a range of from 153° to 156° C. for a period of 3 hours, the pressure dropping during the run until a final pressure of 154 atmospheres was reached. At the end of the 3 hour period heating was discontinued and the autoclave was allowed to return to room temperature. The excess pressure was discharged, the autoclave was opened, and the reaction products recovered therefrom. The products were subjected to preparative gas-liquid chromatography followed by infrared nuclear magnetic resonance and mass spectroscopies. The analysis determined that there had been a 90.72% conversion of ethylene with an 83.4% selectivity to alkyl pyridines, 2-ethyl-3,4-dimethylpyridine being the main product.

We claim as our invention:

1. A process for the preparation of alkyl pyridine which comprises reacting a mixture of ethylene, carbon monoxide, hydrogen and ammonia in the presence of a metal phthalocyanine catalyst complex in which the metallic portion is selected from the transition metals of Groups IB and VIII of the Periodic Table, and recovering the resultant alkyl pyridine.

2. The process as set forth in claim 1 in which the reaction conditions include a temperature in the range of from about 50° to about 300° C. and a pressure in the range of from about 10 to about 300 atmospheres.

3. The process as set forth in claim 1 in which said catalyst complex is cobalt phthalocyanine.

4. The process as set forth in claim 1 in which said catalyst complex is chlororhodium phthalocyanine tetrasulfonate.

5. The process as set forth in claim 1 in which said catalyst complex is ruthenium phthalocyanine.

6. The process as set forth in claim 1 in which the mole ratio of ammonia to ethylene in the mixture is in a range of from about 1:1 to about 5:1 moles of ammonia per mole of ethylene.

7. The process as set forth in claim 1 in which the mole ratio of carbon monoxide to ethylene in the mixture is in a range of from about 1:1 to about 2:1 moles of carbon monoxide per mole of ethylene.

8. The process as set forth in claim 1 in which said alkyl pyridine is dimethyl ethylenepyridine.

9. The process as set forth in claim 1 in which said alkyl pyridine is a mixture of dimethylpyridines.

* * * * *